United States Patent [19]

Gill et al.

[11] Patent Number: 5,504,192
[45] Date of Patent: Apr. 2, 1996

[54] HUMAN INSULIN RECEPTOR ENDOCYTIC CODE BINDING PROTEIN

[75] Inventors: Gordon N. Gill; Rui-Yun Wu, both of La Jolla, Calif.

[73] Assignee: The Regents of the University of California, Oakland, Calif.

[21] Appl. No.: 166,316

[22] Filed: Dec. 13, 1993

[51] Int. Cl.⁶ .......................... C07K 14/435; C12N 15/09
[52] U.S. Cl. .......................... 530/350; 530/303; 530/324; 435/69.1
[58] Field of Search .......................... 435/69.1; 530/350, 530/324, 303

[56] References Cited

PUBLICATIONS

Wu et al., Molecular Biology of the Cell, vol. 4 (Suppl), p. 117A 1993.

*Primary Examiner*—Garnette D. Draper
*Assistant Examiner*—Sally P. Teng
*Attorney, Agent, or Firm*—Fish & Richardson

[57] ABSTRACT

A novel protein that binds to the endocytic code of the human insulin receptor (hIR), which mediates receptor endocytosis, polynucleotides and methods of use are described.

2 Claims, 8 Drawing Sheets

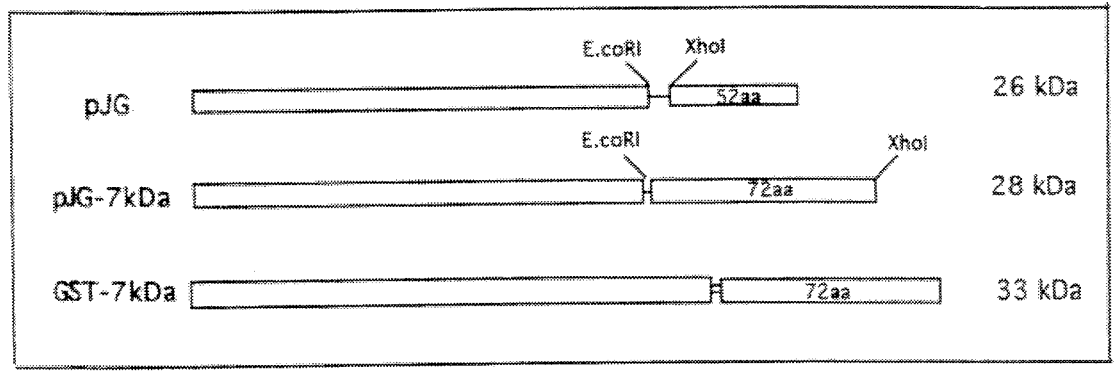
FIG. 2A
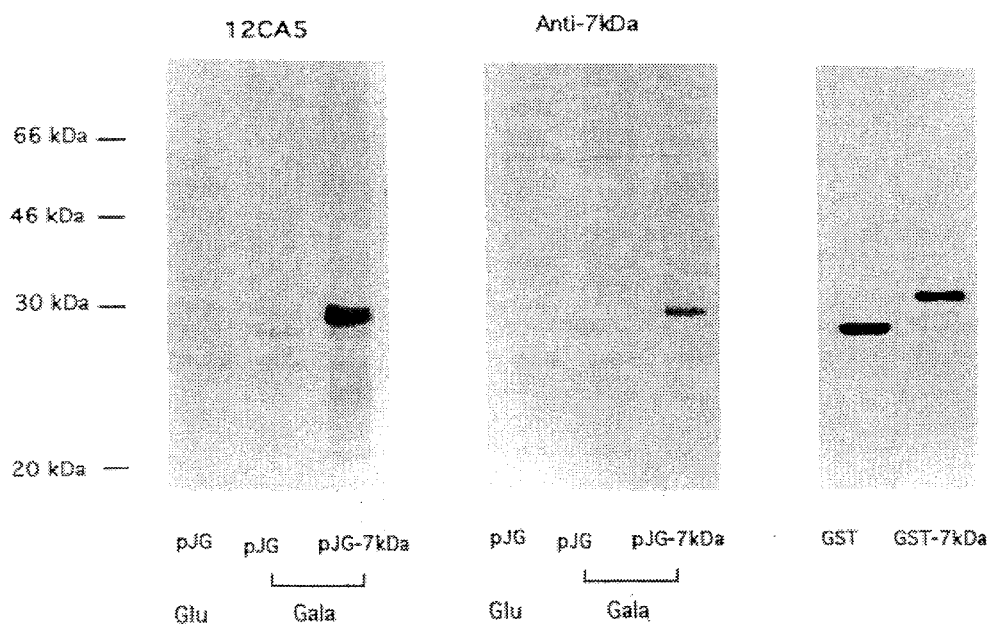
FIG. 2B  FIG. 2C  FIG. 2D

Total RNA

28S →
18S →

N18  SKNSH  IMR32  JURKAT  Mouse Tissues: Liver Kidney Cortex Lung

28S →
18S →

HELA  HEP  ATT20  SKNMC  F9  PC12  RAT1  CV1

FIG. 3A

SKNMC  HELA 4.40kb —
2.37kb —
1.35kb —

Southern Blot
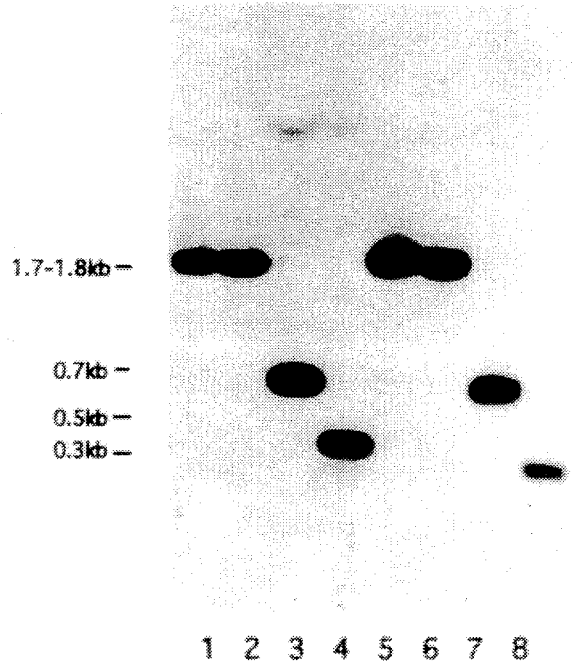
FIG. 4
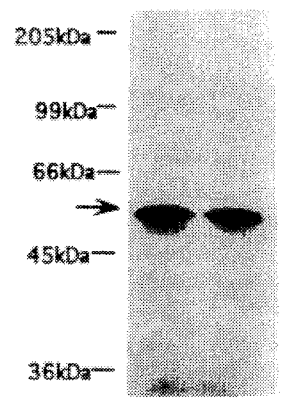
FIG. 7
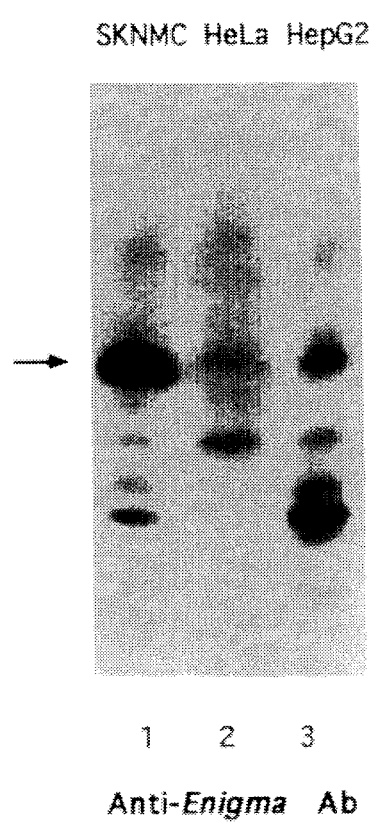
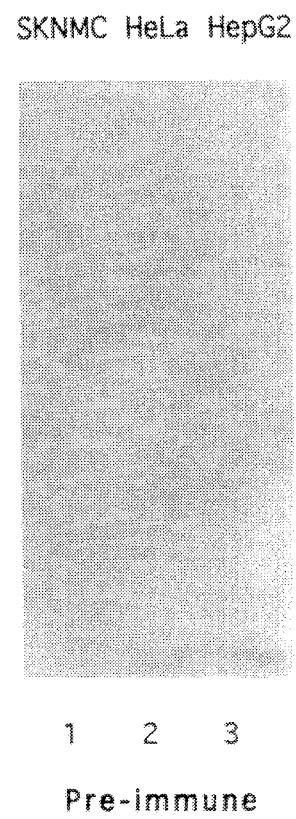
FIG. 8

| | |
|---|---|
| ATG GAT TCC TTC AAA GTA GTG CTG GAG GGG CCA GCA CCT TGG GGC TTC<br>Met Asp Ser Phe Lys Val Val Leu Glu Gly Pro Ala Pro Trp Gly Phe<br>1                  5                  10                15 | 48 |
| CGG CTG CAA GGG GGC AAG GAC TTC AAT GTG CCC CTC TCC ATT TCC CGG<br>Arg Leu Gln Gly Gly Lys Asp Phe Asn Val Pro Leu Ser Ile Ser Arg<br>              20                25               30 | 96 |
| CTC ACT CCT GGG GGC AAA GCG GCG CAG CGG AGT GGC GTG GGT GAC TGG<br>Leu Thr Pro Gly Gly Lys Ala Ala Gln Arg Ser Gly Val Gly Asp Trp<br>        35                40               45 | 144 |
| GTG CTG AGC ATC GAT GGC GAG AAT GCG GGT AGC CTC ACA CAC ATC GAA<br>Val Leu Ser Ile Asp Gly Glu Asn Ala Gly Ser Leu Thr His Ile Glu<br>    50                55               60 | 192 |
| GCT CAG AAC AAG ATC CGG GCC TGC GGG GAA GCG CCT CAG CCT GGG CCT<br>Ala Gln Asn Lys Ile Arg Ala Cys Gly Glu Ala Pro Gln Pro Gly Pro<br>65                  70               75               80 | 240 |
| CAG CAG GGC CCA GCC GGT TCA GAG CAA ACC GCA GAA GGC CTC CGC CCC<br>Gln Gln Gly Pro Ala Gly Ser Glu Gln Thr Ala Glu Gly Leu Arg Pro<br>              85                90               95 | 288 |
| CGC CGC GGA CCC TCC GCG TAC ACC TTT GCA CCC AGC GTC TCC CTC AAC<br>Arg Arg Gly Pro Ser Ala Tyr Thr Phe Ala Pro Ser Val Ser Leu Asn<br>            100               105             110 | 336 |
| AAG ACG GCC CAA CCC TTT GGG CCC CCC GGC GCT GAC AGC CCC CCG CAG<br>Lys Thr Ala Gln Pro Phe Gly Pro Pro Gly Ala Asp Ser Pro Pro Gln<br>        115               120             125 | 384 |
| CAG AAT GGA CAG CCG CTC CGA CCG CTG GTC CCA GAT GCC AGC AAG CAG<br>Gln Asn Gly Gln Pro Leu Arg Pro Leu Val Pro Asp Ala Ser Lys Gln<br>    130                135             140 | 432 |
| CGG CTG ATG GAG AAC ACA GAG GAC TGG CGG CCG CGG CCG GGA CAG GCC<br>Arg Leu Met Glu Asn Thr Glu Asp Trp Arg Pro Arg Pro Gly Gln Ala<br>145                 150              155              160 | 480 |
| AGT CGC GTT CCT TCC GCA TCC TTG CCC ACC TCA CAG GCT CCG AGT TCA<br>Ser Arg Val Pro Ser Ala Ser Leu Pro Thr Ser Gln Ala Pro Ser Ser<br>            165               170             175 | 528 |
| TGC AAG ACC CCG GAT GAG GAG CAC CTG AAG AAA TCA AGC CAG GTG CCA<br>Cys Lys Thr Pro Asp Glu Glu His Leu Lys Lys Ser Ser Gln Val Pro<br>              180             185             190 | 576 |
| GAC AGA AGC CCC AGC CCC AGC CTC ATC TAC ACC CCA GGA GCC CTG GCC<br>Asp Arg Ser Pro Ser Pro Ser Leu Ile Tyr Thr Pro Gly Ala Leu Ala<br>        195               200             205 | 624 |
| TGG CCC TAC CGC CCC CAG CCC TAC CAG CCG CCC GCC CTG GGC TGT GGA<br>Trp Pro Tyr Arg Pro Gln Pro Tyr Gln Pro Pro Ala Leu Gly Cys Gly<br>    210                215             220 | 672 |
| CCC TGC GTT TGC CGA GCG CTA TGC CCC GGA CAA AAC GAG CAC AGT GCT<br>Pro Cys Val Cys Arg Ala Leu Cys Pro Gly Gln Asn Glu His Ser Ala | 720 |

FIG. 5A

```
GAC CCA CAC AGC CAG CCA GCC ACG CCC ACG CCG CTG CAG AGC CGC ACC        768
Asp Pro His Ser Gln Pro Ala Thr Pro Thr Pro Leu Gln Ser Arg Thr
                245                 250                 255

TCC ATT GTG CAG GCA GCT GCC GGA GGG GTG CCA GGA GGG GGC AGC AAC        816
Ser Ile Val Gln Ala Ala Ala Gly Gly Val Pro Gly Gly Gly Ser Asn
                260                 265                 270

AAC GGC AAG ACT CCC GTG TGT CAC CAG TGC CAC AAG GTC ATC CGG GGC        864
Asn Gly Lys Thr Pro Val Cys His Gln Cys His Lys Val Ile Arg Gly
            275                 280                 285

CGC TAC CTG GTG GCG CTG GGC CAC GCG TAC CAC CCG GAG GAG TTT GTG        912
Arg Tyr Leu Val Ala Leu Gly His Ala Tyr His Pro Glu Glu Phe Val
        290                 295                 300

TGT AGC CAG TGT GGG AAG GTC CTG GAA GAG GGT GGC TTC TTT GAG GAG        960
Cys Ser Gln Cys Gly Lys Val Leu Glu Glu Gly Gly Phe Phe Glu Glu
305                 310                 315                 320

AAG GGC GCC ATC TTC TGC CCA CCA TGC TAT GAC GTG CGC TAT GCA CCC       1008
Lys Gly Ala Ile Phe Cys Pro Pro Cys Tyr Asp Val Arg Tyr Ala Pro
                325                 330                 335

AGC TGT GCC AAG TGC AAG AAG AAG ATT ACA GGC GAG ATC ATG CAC GCC       1056
Ser Cys Ala Lys Cys Lys Lys Lys Ile Thr Gly Glu Ile Met His Ala
                340                 345                 350

CTG AAG ATG ACC TGG CAC GTG CAC TGC TTT ACC TGT GCT GCC TGC AAG       1104
Leu Lys Met Thr Trp His Val His Cys Phe Thr Cys Ala Ala Cys Lys
                355                 360                 365

ACG CCC ATC CGG AAC AGG GCC TTC TAC ATG GAG GAG GGC GTG CCC TAT       1152
Thr Pro Ile Arg Asn Arg Ala Phe Tyr Met Glu Glu Gly Val Pro Tyr
        370                 375                 380

TGC GAG CGA GAC TAT GAG AAG ATG TTT GGC ACG AAA TGC CAT GGC TGT       1200
Cys Glu Arg Asp Tyr Glu Lys Met Phe Gly Thr Lys Cys His Gly Cys
385                 390                 395                 400

GAC TTC AAG ATC GAC GCT GGG GAC CGC TTC CTG GAG GCC CTG GGC TTC       1248
Asp Phe Lys Ile Asp Ala Gly Asp Arg Phe Leu Glu Ala Leu Gly Phe
                405                 410                 415

AGC TGG CAT GAC ACC TGC TTC GTC TGT GCG ATA TGT CAG ATC AAC CTG       1296
Ser Trp His Asp Thr Cys Phe Val Cys Ala Ile Cys Gln Ile Asn Leu
                420                 425                 430

GAA GGA AAG ACC TTC TAC TCC AAG AAG GAC AGG CCT CTC TGC AAG AGC       1344
Glu Gly Lys Thr Phe Tyr Ser Lys Lys Asp Arg Pro Leu Cys Lys Ser
                435                 440                 445

CAT GCC TTC TCT CAT GTG TGAGCCCCTT CTGCCCACAG CTGCCGCGGT              1392
His Ala Phe Ser His Val
        450
```

FIG. 5B

MDSFKVVLEGPAPWGFRLQGGKDFNVPLSISRLTPGGKAAQRSGVGDWVLSIDGENAGSLTHIEAQNKIR
ACGEAPQPGPQQGPAGSEQTAEGLRPRRGPSAYTFAPSVSLNKTAQPFGPPGADSPPQQNGQPLRPLVPD
ASKQRLMENTEDWRPRPGQASRVPSASLPTSQAPSSCKTPDEEHLKKSSQVPDRSPSPSLIYTPGALAWP
YRPQPYQPPALGCGPCVCRALCPGQNEHSADPHSQPATPTPLQSRTSIVQAAAGGVPGGGSNNGKTPVCH
QCHKVIRGRYLVALGHAYHPEEFVCSQCGKVLEEGGFFEEKGAIFCPPCYDVRYAPSCAKCKKKITGEIM
HALKMTWHVHCFTCAACKTPIRNRAFYMEEGVPY<u>CERDYEKMFGTKCHGCDFKIDAGDRFLEALG</u>FSWHD
<u>TCFVCAICQINLEGKTFYSKKDRPLCKSHAFSHV</u>

FIG. 6

SPECIFIC INTERACTION BETWEEN ENDOCYTIC CODES AND *ENIGMA*

| Endocytic Codes | | Activity | |
|---|---|---|---|
| Exon 16/IR | QPDGPLGPLYASSNPEYLSASD | 100% | |
| APLAmut/IR | QPDGPLAPLAASSNPEYLSASD | - | |
| APEAmut/IR | QPDGPLGPLYASSAPEALSASD | 60% | |
| double-mut/IR | QPDGPLAPLAASSAPEALSASD | - | |
| Exon 16/IGF1-R | NNSRLGNGVLYASVNPEYFSASD | - | |
| ΔNPEY/IGF1-R | NNSRLGNGVLYASVFSASD | - | |
| 993-1022/EGF-R | LIPQQGPPSSPSTSRTPLLSSLSATSNNS | - | |
| 1022-1186/EGF-R | ----NPVY---NPEY---NPRY--- | - | |
| 993-1022NNAYF | LIPNNAYFSSPSTSRTPLLSSLSATSNNS | - | |
| 730-780/LDL-R | ----------NPVY------------ | - | |
| 1-61/Tf-R | ----------PLSYTRF---------- | - | |
| HTH/NNAYF | KQKVVKLNNAYFMFSHRINNAYFKQKVVKL | 3% | |

FIG. 9

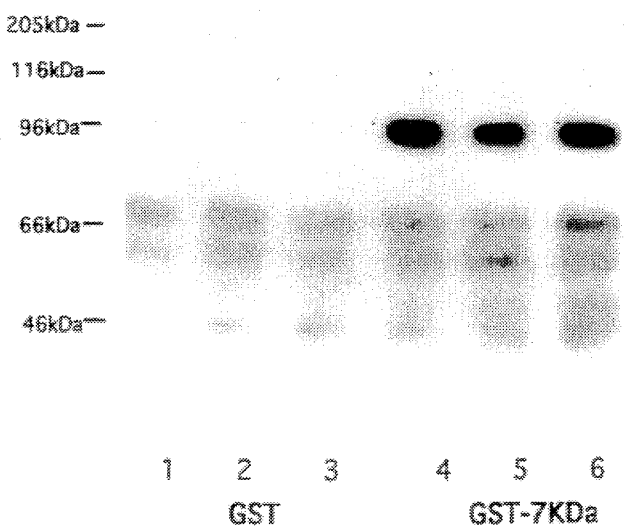

Interaction between *Enigma* and hIR *In vitro*

FIG. 10

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
        ( A ) LENGTH: 1597 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 1..1362

( x i ) SEQUENCE DESCRIPTION: SEQ ID NO:1:

```
ATG  GAT  TCC  TTC  AAA  GTA  GTG  CTG  GAG  GGG  CCA  GCA  CCT  TGG  GGC  TTC        48
Met  Asp  Ser  Phe  Lys  Val  Val  Leu  Glu  Gly  Pro  Ala  Pro  Trp  Gly  Phe
 1                  5                        10                       15

CGG  CTG  CAA  GGG  GGC  AAG  GAC  TTC  AAT  GTG  CCC  CTC  TCC  ATT  TCC  CGG        96
Arg  Leu  Gln  Gly  Gly  Lys  Asp  Phe  Asn  Val  Pro  Leu  Ser  Ile  Ser  Arg
                 20                        25                       30

CTC  ACT  CCT  GGG  GGC  AAA  GCG  GCG  CAG  CGG  AGT  GGC  GTG  GGT  GAC  TGG       144
Leu  Thr  Pro  Gly  Gly  Lys  Ala  Ala  Gln  Arg  Ser  Gly  Val  Gly  Asp  Trp
            35                        40                   45

GTG  CTG  AGC  ATC  GAT  GGC  GAG  AAT  GCG  GGT  AGC  CTC  ACA  CAC  ATC  GAA       192
Val  Leu  Ser  Ile  Asp  Gly  Glu  Asn  Ala  Gly  Ser  Leu  Thr  His  Ile  Glu
       50                        55                   60

GCT  CAG  AAC  AAG  ATC  CGG  GCC  TGC  GGG  GAA  GCG  CCT  CAG  CCT  GGG  CCT       240
Ala  Gln  Asn  Lys  Ile  Arg  Ala  Cys  Gly  Glu  Ala  Pro  Gln  Pro  Gly  Pro
 65                 70                        75                       80

CAG  CAG  GGC  CCA  GCC  GGT  TCA  GAG  CAA  ACC  GCA  GAA  GGC  CTC  CGC  CCC       288
Gln  Gln  Gly  Pro  Ala  Gly  Ser  Glu  Gln  Thr  Ala  Glu  Gly  Leu  Arg  Pro
                 85                        90                       95

CGC  CGC  GGA  CCC  TCC  GCG  TAC  ACC  TTT  GCA  CCC  AGC  GTC  TCC  CTC  AAC       336
Arg  Arg  Gly  Pro  Ser  Ala  Tyr  Thr  Phe  Ala  Pro  Ser  Val  Ser  Leu  Asn
                100                       105                      110
```

| | | | | | | | | | | | | | | | | |
|---|---|---|---|---|---|---|---|---|---|---|---|---|---|---|---|---|
| AAG | ACG | GCC | CAA | CCC | TTT | GGG | CCC | CCC | GGC | GCT | GAC | AGC | CCC | CCG | CAG | 384 |
| Lys | Thr | Ala | Gln | Pro | Phe | Gly | Pro | Pro | Gly | Ala | Asp | Ser | Pro | Pro | Gln | |
| | | 115 | | | | 120 | | | | | | 125 | | | | |
| CAG | AAT | GGA | CAG | CCG | CTC | CGA | CCG | CTG | GTC | CCA | GAT | GCC | AGC | AAG | CAG | 432 |
| Gln | Asn | Gly | Gln | Pro | Leu | Arg | Pro | Leu | Val | Pro | Asp | Ala | Ser | Lys | Gln | |
| | 130 | | | | | 135 | | | | | | 140 | | | | |
| CGG | CTG | ATG | GAG | AAC | ACA | GAG | GAC | TGG | CGG | CCG | CGG | CCG | GGA | CAG | GCC | 480 |
| Arg | Leu | Met | Glu | Asn | Thr | Glu | Asp | Trp | Arg | Pro | Arg | Pro | Gly | Gln | Ala | |
| 145 | | | | | 150 | | | | | 155 | | | | | 160 | |
| AGT | CGC | GTT | CCT | TCC | GCA | TCC | TTG | CCC | ACC | TCA | CAG | GCT | CCG | AGT | TCA | 528 |
| Ser | Arg | Val | Pro | Ser | Ala | Ser | Leu | Pro | Thr | Ser | Gln | Ala | Pro | Ser | Ser | |
| | | | | 165 | | | | | 170 | | | | | 175 | | |
| TGC | AAG | ACC | CCG | GAT | GAG | GAG | CAC | CTG | AAG | AAA | TCA | AGC | CAG | GTG | CCA | 576 |
| Cys | Lys | Thr | Pro | Asp | Glu | Glu | His | Leu | Lys | Lys | Ser | Ser | Gln | Val | Pro | |
| | | | 180 | | | | | 185 | | | | | 190 | | | |
| GAC | AGA | AGC | CCC | AGC | CCC | AGC | CTC | ATC | TAC | ACC | CCA | GGA | GCC | CTG | GCC | 624 |
| Asp | Arg | Ser | Pro | Ser | Pro | Ser | Leu | Ile | Tyr | Thr | Pro | Gly | Ala | Leu | Ala | |
| | | 195 | | | | | 200 | | | | | 205 | | | | |
| TGG | CCC | TAC | CGC | CCC | CAG | CCC | TAC | CAG | CCG | CCC | GCC | CTG | GGC | TGT | GGA | 672 |
| Trp | Pro | Tyr | Arg | Pro | Gln | Pro | Tyr | Gln | Pro | Pro | Ala | Leu | Gly | Cys | Gly | |
| | 210 | | | | | 215 | | | | | | 220 | | | | |
| CCC | TGC | GTT | TGC | CGA | GCG | CTA | TGC | CCC | GGA | CAA | AAC | GAG | CAC | AGT | GCT | 720 |
| Pro | Cys | Val | Cys | Arg | Ala | Leu | Cys | Pro | Gly | Gln | Asn | Glu | His | Ser | Ala | |
| 225 | | | | | 230 | | | | | 235 | | | | | 240 | |
| GAC | CCA | CAC | AGC | CAG | CCA | GCC | ACG | CCC | ACG | CCG | CTG | CAG | AGC | CGC | ACC | 768 |
| Asp | Pro | His | Ser | Gln | Pro | Ala | Thr | Pro | Thr | Pro | Leu | Gln | Ser | Arg | Thr | |
| | | | | 245 | | | | | 250 | | | | | 255 | | |
| TCC | ATT | GTG | CAG | GCA | GCT | GCC | GGA | GGG | GTG | CCA | GGA | GGG | GGC | AGC | AAC | 816 |
| Ser | Ile | Val | Gln | Ala | Ala | Ala | Gly | Gly | Val | Pro | Gly | Gly | Gly | Ser | Asn | |
| | | | 260 | | | | | 265 | | | | | 270 | | | |
| AAC | GGC | AAG | ACT | CCC | GTG | TGT | CAC | CAG | TGC | CAC | AAG | GTC | ATC | CGG | GGC | 864 |
| Asn | Gly | Lys | Thr | Pro | Val | Cys | His | Gln | Cys | His | Lys | Val | Ile | Arg | Gly | |
| | | 275 | | | | | 280 | | | | | 285 | | | | |
| CGC | TAC | CTG | GTG | GCG | CTG | GGC | CAC | GCG | TAC | CAC | CCG | GAG | GAG | TTT | GTG | 912 |
| Arg | Tyr | Leu | Val | Ala | Leu | Gly | His | Ala | Tyr | His | Pro | Glu | Glu | Phe | Val | |
| | 290 | | | | | 295 | | | | | 300 | | | | | |
| TGT | AGC | CAG | TGT | GGG | AAG | GTC | CTG | GAA | GAG | GGT | GGC | TTC | TTT | GAG | GAG | 960 |
| Cys | Ser | Gln | Cys | Gly | Lys | Val | Leu | Glu | Glu | Gly | Gly | Phe | Phe | Glu | Glu | |
| 305 | | | | | 310 | | | | | 315 | | | | | 320 | |
| AAG | GGC | GCC | ATC | TTC | TGC | CCA | CCA | TGC | TAT | GAC | GTG | CGC | TAT | GCA | CCC | 1008 |
| Lys | Gly | Ala | Ile | Phe | Cys | Pro | Pro | Cys | Tyr | Asp | Val | Arg | Tyr | Ala | Pro | |
| | | | | 325 | | | | | 330 | | | | | 335 | | |
| AGC | TGT | GCC | AAG | TGC | AAG | AAG | AAG | ATT | ACA | GGC | GAG | ATC | ATG | CAC | GCC | 1056 |
| Ser | Cys | Ala | Lys | Cys | Lys | Lys | Lys | Ile | Thr | Gly | Glu | Ile | Met | His | Ala | |
| | | | 340 | | | | | 345 | | | | | 350 | | | |
| CTG | AAG | ATG | ACC | TGG | CAC | GTG | CAC | TGC | TTT | ACC | TGT | GCT | GCC | TGC | AAG | 1104 |
| Leu | Lys | Met | Thr | Trp | His | Val | His | Cys | Phe | Thr | Cys | Ala | Ala | Cys | Lys | |
| | | 355 | | | | | 360 | | | | | 365 | | | | |
| ACG | CCC | ATC | CGG | AAC | AGG | GCC | TTC | TAC | ATG | GAG | GAG | GGC | GTG | CCC | TAT | 1152 |
| Thr | Pro | Ile | Arg | Asn | Arg | Ala | Phe | Tyr | Met | Glu | Glu | Gly | Val | Pro | Tyr | |
| | 370 | | | | | 375 | | | | | 380 | | | | | |
| TGC | GAG | CGA | GAC | TAT | GAG | AAG | ATG | TTT | GGC | ACG | AAA | TGC | CAT | GGC | TGT | 1200 |
| Cys | Glu | Arg | Asp | Tyr | Glu | Lys | Met | Phe | Gly | Thr | Lys | Cys | His | Gly | Cys | |
| 385 | | | | | 390 | | | | | 395 | | | | | 400 | |
| GAC | TTC | AAG | ATC | GAC | GCT | GGG | GAC | CGC | TTC | CTG | GAG | GCC | CTG | GGC | TTC | 1248 |
| Asp | Phe | Lys | Ile | Asp | Ala | Gly | Asp | Arg | Phe | Leu | Glu | Ala | Leu | Gly | Phe | |
| | | | | 405 | | | | | 410 | | | | | 415 | | |
| AGC | TGG | CAT | GAC | ACC | TGC | TTC | GTC | TGT | GCG | ATA | TGT | CAG | ATC | AAC | CTG | 1296 |
| Ser | Trp | His | Asp | Thr | Cys | Phe | Val | Cys | Ala | Ile | Cys | Gln | Ile | Asn | Leu | |
| | | | 420 | | | | | 425 | | | | | 430 | | | |

```
GAA GGA AAG ACC TTC TAC TCC AAG AAG GAC AGG CCT CTC TGC AAG AGC      1344
Glu Gly Lys Thr Phe Tyr Ser Lys Lys Asp Arg Pro Leu Cys Lys Ser
        435                 440                 445

CAT GCC TTC TCT CAT GTG TGAGCCCCTT CTGCCCACAG CTGCCGCGGT             1392
His Ala Phe Ser His Val
        450

GGCCCCTAGC CTGAGGGGCC TGGAGTCGTG GCCCCTGCAT TTCTGGGTAG GGCTGGCAAT    1452

GGTTGCCTTA ACCCTGGCTC CTGGCCCGAG CCTGGGCTCC CTGGCCCTGC CCCACCCACC    1512

TTATCCTCCC ACCCCACTCC CTCCACCACC ACAGCACACC GGTGCTGGCC ACACCAGCCC    1572

CCTTTCACCT CCAGTGCCAC AATAA                                          1597
```

( 2 ) INFORMATION FOR SEQ ID NO:2:

( i ) SEQUENCE CHARACTERISTICS:
        ( A ) LENGTH: 454 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Asp Ser Phe Lys Val Val Leu Glu Gly Pro Ala Pro Trp Gly Phe
 1               5                  10                  15

Arg Leu Gln Gly Gly Lys Asp Phe Asn Val Pro Leu Ser Ile Ser Arg
            20                  25                  30

Leu Thr Pro Gly Gly Lys Ala Ala Gln Arg Ser Gly Val Gly Asp Trp
        35                  40                  45

Val Leu Ser Ile Asp Gly Glu Asn Ala Gly Ser Leu Thr His Ile Glu
    50                  55                  60

Ala Gln Asn Lys Ile Arg Ala Cys Gly Glu Ala Pro Gln Pro Gly Pro
 65                  70                  75                  80

Gln Gln Gly Pro Ala Gly Ser Glu Gln Thr Ala Glu Gly Leu Arg Pro
                85                  90                  95

Arg Arg Gly Pro Ser Ala Tyr Thr Phe Ala Pro Ser Val Ser Leu Asn
            100                 105                 110

Lys Thr Ala Gln Pro Phe Gly Pro Pro Gly Ala Asp Ser Pro Pro Gln
        115                 120                 125

Gln Asn Gly Gln Pro Leu Arg Pro Leu Val Pro Asp Ala Ser Lys Gln
    130                 135                 140

Arg Leu Met Glu Asn Thr Glu Asp Trp Arg Pro Arg Pro Gly Gln Ala
145                 150                 155                 160

Ser Arg Val Pro Ser Ala Ser Leu Pro Thr Ser Gln Ala Pro Ser Ser
                165                 170                 175

Cys Lys Thr Pro Asp Glu Glu His Leu Lys Lys Ser Ser Gln Val Pro
            180                 185                 190

Asp Arg Ser Pro Ser Pro Ser Leu Ile Tyr Thr Pro Gly Ala Leu Ala
        195                 200                 205

Trp Pro Tyr Arg Pro Gln Pro Tyr Gln Pro Pro Ala Leu Gly Cys Gly
    210                 215                 220

Pro Cys Val Cys Arg Ala Leu Cys Pro Gly Gln Asn Glu His Ser Ala
225                 230                 235                 240

Asp Pro His Ser Gln Pro Ala Thr Pro Thr Pro Leu Gln Ser Arg Thr
                245                 250                 255

Ser Ile Val Gln Ala Ala Ala Gly Gly Val Pro Gly Gly Gly Ser Asn
            260                 265                 270
```

```
Asn Gly Lys Thr Pro Val Cys His Gln Cys His Lys Val Ile Arg Gly
    275             280                 285

Arg Tyr Leu Val Ala Leu Gly His Ala Tyr His Pro Glu Glu Phe Val
    290             295             300

Cys Ser Gln Cys Gly Lys Val Leu Glu Glu Gly Gly Phe Phe Glu Glu
305             310                 315                     320

Lys Gly Ala Ile Phe Cys Pro Pro Cys Tyr Asp Val Arg Tyr Ala Pro
                325             330                 335

Ser Cys Ala Lys Cys Lys Lys Lys Ile Thr Gly Glu Ile Met His Ala
            340             345                 350

Leu Lys Met Thr Trp His Val His Cys Phe Thr Cys Ala Ala Cys Lys
        355             360                 365

Thr Pro Ile Arg Asn Arg Ala Phe Tyr Met Glu Glu Gly Val Pro Tyr
    370             375             380

Cys Glu Arg Asp Tyr Glu Lys Met Phe Gly Thr Lys Cys His Gly Cys
385             390                 395                     400

Asp Phe Lys Ile Asp Ala Gly Asp Arg Phe Leu Glu Ala Leu Gly Phe
                405             410                 415

Ser Trp His Asp Thr Cys Phe Val Cys Ala Ile Cys Gln Ile Asn Leu
            420             425                 430

Glu Gly Lys Thr Phe Tyr Ser Lys Lys Asp Arg Pro Leu Cys Lys Ser
        435             440                 445

His Ala Phe Ser His Val
    450
```

(2) INFORMATION FOR SEQ ID NO:3:

( i ) SEQUENCE CHARACTERISTICS:
        ( A ) LENGTH: 70 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1..70

( x i ) SEQUENCE DESCRIPTION: SEQ ID NO:3:

```
Cys Glu Arg Asp Tyr Glu Lys Met Phe Gly Thr Lys Cys His Gly Cys
1               5                   10                  15

Asp Phe Lys Ile Asp Ala Gly Asp Arg Phe Leu Glu Ala Leu Gly Phe
                20              25                  30

Ser Trp His Asp Thr Cys Phe Val Cys Ala Ile Cys Gln Ile Asn Leu
            35              40                  45

Glu Gly Lys Thr Phe Tyr Ser Lys Lys Asp Arg Pro Leu Cys Lys Ser
        50              55                  60

His Ala Phe Ser His Val
65              70
```

(2) INFORMATION FOR SEQ ID NO:4:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:

( A ) NAME/KEY: CDS
( B ) LOCATION: 1..26

( x i ) SEQUENCE DESCRIPTION: SEQ ID NO:4:

TTTAGAATTC CAGCCAGATG GGCCGC  26

( 2 ) INFORMATION FOR SEQ ID NO:5:

( i ) SEQUENCE CHARACTERISTICS:
( A ) LENGTH: 26 base pairs
( B ) TYPE: nucleic acid
( C ) STRANDEDNESS: single
( D ) TOPOLOGY: linear ( i i ) MOLECULE TYPE: DNA (genomic)

( i x ) FEATURE:
( A ) NAME/KEY: CDS
( B ) LOCATION: 1..26

( x i ) SEQUENCE DESCRIPTION: SEQ ID NO:5:

CGATGGATCC ATCACTGGCA CTGAGA  26

( 2 ) INFORMATION FOR SEQ ID NO:6:

( i ) SEQUENCE CHARACTERISTICS:
( A ) LENGTH: 4 amino acids
( B ) TYPE: amino acid
( C ) STRANDEDNESS: single
( D ) TOPOLOGY: linear ( i i ) MOLECULE TYPE: peptide ( i x ) FEATURE:
( A ) NAME/KEY: Peptide
( B ) LOCATION: 1..4

( x i ) SEQUENCE DESCRIPTION: SEQ ID NO:6:

Gly Pro Leu Tyr
1

( 2 ) INFORMATION FOR SEQ ID NO:7:

( i ) SEQUENCE CHARACTERISTICS:
( A ) LENGTH: 4 amino acids
( B ) TYPE: amino acid
( C ) STRANDEDNESS: single
( D ) TOPOLOGY: linear ( i i ) MOLECULE TYPE: peptide ( i x ) FEATURE:
( A ) NAME/KEY: Peptide
( B ) LOCATION: 1..4

( x i ) SEQUENCE DESCRIPTION: SEQ ID NO:7:

Ala Pro Leu Ala
1

( 2 ) INFORMATION FOR SEQ ID NO:8:

( i ) SEQUENCE CHARACTERISTICS:
( A ) LENGTH: 4 amino acids
( B ) TYPE: amino acid
( C ) STRANDEDNESS: single
( D ) TOPOLOGY: linear ( i i ) MOLECULE TYPE: peptide ( i x ) FEATURE:
( A ) NAME/KEY: Peptide
( B ) LOCATION: 1..4

(x i) SEQUENCE DESCRIPTION: SEQ ID NO:8:

Asn Pro Glu Tyr
1

(2) INFORMATION FOR SEQ ID NO:9:

(i) SEQUENCE CHARACTERISTICS:
    (A) LENGTH: 4 amino acids
    (B) TYPE: amino acid
    (C) STRANDEDNESS: single
    (D) TOPOLOGY: linear (i i) MOLECULE TYPE: peptide (i x) FEATURE:
    (A) NAME/KEY: Peptide
    (B) LOCATION: 1..4

(x i) SEQUENCE DESCRIPTION: SEQ ID NO:9:

Ala Pro Glu Ala
1

HUMAN INSULIN RECEPTOR ENDOCYTIC CODE BINDING PROTEIN

BACKGROUND OF THE INVENTION

1. Field of the Invention

This invention relates generally to endocytosis of cell surface receptors and specifically to a novel protein which recognizes and binds to the endocytic code of the human insulin receptor and uses therefor.

2. Description of Related Art

Cell surface receptors have been broadly divided into class I receptors, which are constitutively located in clatharin coated pits under basal conditions, and class II receptors, which move from non-coated to coated regions of the plasma membrane when stimulated by ligand (Goldstein, et al., *Ann. Rev. Cell Biol.*, 1:1–39, 1985). The preferential localization of class I receptor to coated pits is presumably dependent on the cytoplasmic domains of these receptors, as mutant receptors lacking this domain are randomly dispersed in the plasma membrane and poorly internalized. Several endocytic component receptors contain aromatic residues near the cytoplasmic face of the membrane, which are necessary for internalization. The $NPVY^{807}$ sequence in the LDL receptor and the sequence $Y^{20}TRF$ required for transferrin receptor internalization are predicted to form tight turns (Collawn, et al., *Cell*, 63:1061, 1990). Furthermore, the introduction of a tyrosine residue immediately distal to residues favoring turn formation in the cytoplasmic tail of glycophorin caused this molecule, normally excluded from coated pits, to be efficiently internalized (Ktistakas, et al., *J. Cell Biol.*, 111:1393, 1990).

The internalization of class II receptors, which include the insulin and EGF receptors, is more complex. They require both intrinsic tyrosine kinase activity and specific amino acid sequences termed the endocytic codes (Russel, et al., *J. Biol. Chem.*, 262:11833, 1987). The insulin receptor is a dimeric, transmembrane glycoprotein consisting of two extracellular α and two transmembrane β-subunits.

The structure and function of the insulin receptor have been thoroughly analyzed after the cloning of the receptor cDNA (Ullrich, et al., *Nature*, 313:756, 1985). There are several structural domains within the receptor, a cysteine-rich domain in the α-subunit, a single transmembrane domain, and a region in the β-subunit with homology to tyrosine-specific protein kinase (Kasuga, M., et al., *Proc. Natl. Acad. Sci U.S.A.*, 80:2137–2141; Ullrich, A., et al., *Nature*, 313:756–761, 1985; Ebina, Y., et al., *Cell*, 40:747–758, 1985). The first step in insulin action involves high affinity binding of ligand to the receptor. This results in the activation of the tyrosine protein kinase located in the cytoplasmic domain of the β-subunit of the receptor, autophosphorylation and phosphorylation on the tyrosine residues of certain cellular proteins, and internalization of the receptor (McClain, D., et al., *J. Biol. Chem.*, 262:14663–14671, 1987; Hari, J., et al., *J. Biol. Chem.* 262:15431–15434, 1987). M-ophological studies have shown that the kinase deficient $IRA^{1018}$ receptor does not enter coated pits in Rat-1 fibroblasts. A mutant receptor which has a deletion of an intact juxtamembrane region retains its insulin binding and insulin-stimulated tyrosine kinase activities but does not exhibit ligand-induced internalization. The ligand-stimulated internalization requires both receptor autophosphorylation and the intact juxtamembrane region which is encoded by exon 16 (Backer, J., et al., *J. Cell Biol.* 115:1535–1545, 1991; Thies, R., et al., *J. Biol. Chem.* 26,5:10132–10137, 1990). his region contains one copy of an NPXY sequence that is required for the endocytosis of class I receptors such as LDL-R and Tf-R.

Specific sequences involved in endocytosis of the human insulin receptor (hIR) have been analyzed by deletion and by point mutation. It was demonstrated that there were two independent sequences involved in endocytosis (Backer, J., et al., *J. Cell Biol.*, 119:831–839, 1992; Rajagopalan, M., et al., *J. Biol. Chem.* 266:23068–23073, 1991). Cells containing a mutant hIR that have a deletion of the 16th exon which encodes 22 amino acids on the cytoplasmic side of the transmembrane region of the receptor β-subunit, still bind insulin and activate as a tyrosine kinase. However, these cells are unable to internalize the hIR (Thies, et al., *J. Biol. Chem.*, 265:10132, 1990). Therefore, the 16th exon encodes a domain necessary for ligand-dependent endocytosis.

Receptors mutated from GPLY to APLA internalized at only 32% of the rate of normal hIR. On the other hand, receptors mutated from NPEY to APEA internalized insulin at 87% of the normal rate. Similar to wild type receptors, both mutant receptors had the ability to bind insulin and undergo autophosphorylation. The information contained in the GPLY and, to a lesser extent, the NPEY sequences are necessary along with tyrosine kinase activity for signaling internalization of the insulin receptor.

Defects subsequent to ligand activation of insulin receptors have been identified as one cause of diabetes mellitus. Therefore, identification of cellular products that recognize and bind the endocytic code of the hIR and mediate endocytosis via that interaction may be essential. Such a cellular component would be a target for therapeutic compounds in order to alter the "trafficking" of the hIR and other cellular receptor molecules. The present invention provides a protein which binds to the functional endocytic code of hIR, thus fulfilling a longfelt need to identify cellular components which regulate hIR turnover.

SUMMARY OF THE INVENTION

The present invention provides a novel polypeptide which is characterized as binding to the endocytic code of the human insulin receptor (hIR); and having an amino acid sequence according to Sequence ID No. 2 and fragments thereof. The invention also includes a synthetic peptide comprising the endocytic code binding region of the protein of the invention which includes the C-terminal 70 amino acids.

In one embodiment, the invention provides a method for identifying a composition which affects the binding of the polypeptide of the invention to the hIR endocytic code, which comprises incubating the composition, the polypeptide and the endocytic code under conditions which allow the components to interact, and measuring the effect of the composition on the binding of the polypeptide to the code.

In a further embodiment, the invention provides a method of treating a cell disorder associated with endocytosis of the insulin receptor comprising administering to a subject with the disorder, a therapeutically effective amount of a composition which modulates the activity of the endocytic code of the receptor.

In yet a further embodiment, the invention provides a method for detecting a a polypeptide which binds to the endocytic code of the human insulin receptor comprising contacting a sample comprising a cell component associated with binding to the endocytic code of the receptor with a composition which binds to the component and measuring the interaction of the composition with the component. Specifically, the method is useful in detecting a neuron-derived cell, such as a neuroblastoma cell.

Finally, the invention provides a kit useful for the detection of a polypeptide which binds to the endocytic code of the human insulin receptor, the kit comprising a carrier means being compartmentalized to receive in close confinement therein one or more containers comprising a container containing a probe specifically reactive with the polypeptide.

BRIEF DESCRIPTION OF THE DRAWINGS

FIG. 1A shows the bait; FIG. 1B shows the activation domain of the prey and the reporter genes; FIG. 1C shows the interaction of the bait and prey and subsequent reporter gene expression.

FIG. 2 is a Western blot showing that the 27 kD fusion protein is reactive with anti-epitope antiserum.

FIG. 2a illustrates the expected protein products from the library expression plasmid alone (upper line), the library plasmid with the in-frame fusion of the positive 7 kDa fragment (middle line), and the GST-7 kDa fusion protein (lower line).

FIG. 2b demonstrates that antibody 12CA5 recognizes the expected 28 kDa fusion protein only under galactose-induction in yeast containing the plasmid that was positive in the 2-hybrid screen.

FIG. 2c shows that this same fusion protein (as in 2b) was recognized by a rabbit antibody generated against the GST-7 kDa fusion protein.

FIG. 2d shows the GST-7 kDa protein used as immunogen.

FIG. 3a (upper) Northern blot analyses for exon 16 binding protein in SKNSH neuroblastoma cells, N18, IMR 32 and Jurkat cells and mouse tissues (liver, kidney, cortex and lung). FIG. 3a (lower) shows HeLa, HEPG2, ATT20, SKNMC, F9, PC12, RAT1, and CV1 cells.

FIG. 3b shows a Northern blot comparing the endocytic code binding protein expression in SKNMC and HeLa cells.

FIG. 4 is a Southern blot showing the full length and partial cDNAs of the endocytic code binding protein from the SKNMC lambda gt11 library.

FIG. 5 is the nucleotide and deduced amino acid sequence for the protein of hIR endocytic code binding protein.

FIG. 6 is the deduced amino acid for the hIR endocytic code binding protein. The C-terminal binding region is underlined.

FIG. 7 is an SDS-PAGE of an in vitro translation product showing that the endocytic code binding protein is about 55 kD.

FIG. 8 is an SDS-PAGE showing reactivity of anti GST-7 kD (Enigma) antisera with SK-N-MC, HeLa and HepG2 cells.

FIG. 9 is a table showing the binding of the hIR endocytic code binding protein of the invention to the endocytic codes of hIR and other receptors.

FIG. 10 is an SDS-PAGE of the interaction between the protein of the invention and the hIR in vitro.

DETAILED DESCRIPTION OF THE INVENTION

Figure 1A:
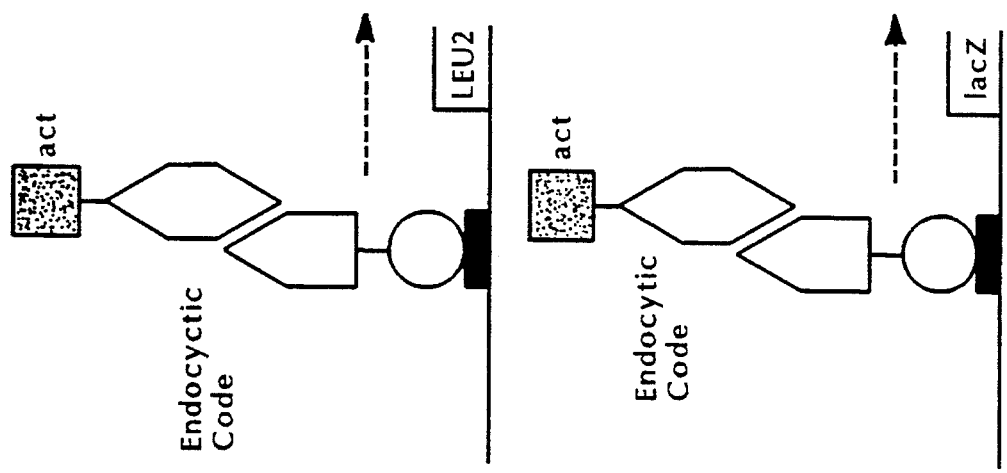
FIG. 1A–C shows a stepwise illustration of the two-hybrid cloning procedure.

The present invention provides a novel protein which binds to a well-defined site on the human insulin receptor (hIR). This site on the hIR is found in exon 16 which encodes 22 amino acids and is in the cytoplasmic domain of the receptor. The region which is defined by GPLY, and to a lesser extent NPEY in exon 16, is referred to as an "endocytic code" and functions to mediate receptor endocytosis. The isolated polypeptide of the invention is characterized by binding to the endocytic code of the human insulin receptor, and having an amino acid sequence according to Sequence ID No. 2, and fragments thereof.

The term "isolated" means any hIR endocytic code binding protein of the present invention, or any gene encoding a hIR endocytic code binding protein, which is essentially free of other polypeptides or genes, respectively, or of other contaminants with which the hIR endocytic code binding protein polypeptide or gene might normally be found in nature.

The invention includes a functional polypeptide, hIR endocytic code binding protein, and functional fragments thereof. As used herein, the term "functional polypeptide" refers to a polypeptide which possesses a biological function or activity which is identified through a defined functional assay and which is associated with a particular biologic, morphologic or phenotypic alteration in the cell. The biological function can vary from a polypeptide fragment as small as an epitope to which an antibody molecule can bind to as large as a polypeptide which is capable of participating in the characteristic induction or programming of phenotypic changes within a cell. A functional polypeptide or fragment of hIR endocytic code binding protein possesses the ability to bind to the endocytic code of hIR, thereby affecting endocytosis of the receptor. A "functional polynucleotide" denotes a polynucleotide which encodes a functional polypeptide as described herein.

Functional polypeptide fragments within the amino acid sequence of Sequence ID No. 2 which bind to an endocytic code can be determined by methods known to those of skill in the art. For example, the endocytic code of interest can be attached to a carrier, such as glutathione-S-transferase (GST) which binds through the GST moiety to glutathione agarose beads. The GST-fusion protein is immobilized on glutathione agarose beads and mixed with the fragments of Sequence ID No. 2 for example. Any unbound fragments are washed away and the fragments bound to the endocytic code are isolated and identified by sequence analysis, for example.

Minor modifications of the hIR endocytic code binding protein primary amino acid sequence may result in proteins which have substantially equivalent activity and binding ability as compared to the hIR endocytic code binding protein described herein. Such modifications may be deliberate, as by site-directed mutagenesis, or may be spontaneous. All of the polypeptides produced by these modifications are included herein as long as the hIR endocytic code binding protein still binds to the endocytic code. Further, deletion of one or more amino acids can also result in a modification of the structure of the resultant molecule without significantly altering its binding ability or activity. This can lead to the development of a smaller active molecule which would have broader utility. For example, one can remove amino terminal amino acids, which do not appear to be required for hIR endocytic code binding protein binding.

The hIR endocytic code binding protein of the invention also includes conservative variations of the polypeptide sequence. The term "conservative variation" as used herein denotes the replacement of an amino acid residue by another, biologically similar residue. Examples of conservative variations include the substitution of one hydrophobic residue such as isoleucine, valine, leucine or methionine for another, or the substitution of one polar residue for another, such as the substitution of arginine for lysine, glutamic for aspartic acids, or glutamine for asparagine, and the like. The term "conservative variation" also includes the use of a substituted amino acid in place of an unsubstituted parent amino acid provided that antibodies raised to the substituted polypeptide also immunoreact with the unsubstituted polypeptide.

The polypeptide of the invention includes a protein which has a molecular weight of about 55 kD as determined by reducing SDS-PAGE. The invention also provides a synthetic peptide which binds to the hIR endocytic code. The amino acid sequence of Sequence ID No. 3, and conservative variations, comprises the synthetic peptide of the invention. This sequence represents amino acids 385–454 of the hIR endocytic code binding protein of the invention, which are the 70, C-terminal amino acids. As used herein, the term "synthetic peptide" denotes a peptide which does not comprise an entire naturally occurring protein molecule. The peptide is "synthetic" in that it may be produced by human intervention using such techniques as chemical synthesis, recombinant genetic techniques, or fragmentation of whole antigen or the like.

Peptides of the invention can be synthesized by such commonly used methods as t-BOC or FMOC protection of alpha-amino groups. Both methods involve stepwise syntheses whereby a single amino acid is added at each step starting from the C terminus of the peptide (See, Coligan, et al., *Current Protocols in Immunology*, Wiley Interscience, 1991, Unit 9). Peptides of the invention can also be synthesized by the well known solid phase peptide synthesis methods described Merrifield, *J. Am. Chem. Soc.*, 85:2149, 1962), and Stewart and Young, *Solid Phase Peptides Synthesis*, (Freeman, San Francisco, 1969, pp.27–62), using a copoly(styrene-divinylbenzene) containing 0.1–1.0 m Mol amines/g polymer. On completion of chemical synthesis, the peptides can be deprotected and cleaved from the polymer by treatment with liquid HF-10% anisole for about ¼–1 hours at 0° C. After evaporation of the reagents, the peptides are extracted from the polymer with 1% acetic acid solution which is then lyophilized to yield the crude material. This can normally be purified by such techniques as gel filtration on Sephadex G-15 using 5% acetic acid as a solvent. Lyophilization of appropriate fractions of the column will yield the homogeneous peptide or peptide derivatives, which can then be characterized by such standard techniques as amino acid analysis, thin layer chromatography, high performance liquid chromatography, ultraviolet absorption spectroscopy, molar rotation, solubility, and quantitated by the solid phase Edman degradation.

The peptide of the invention can be synthesized by biological methods using expression of the protein in mammalian cells, insect cells, yeast and bacteria. Protein expression can be optimized for each system by well-established methods. Protein can be purified by standard methods (Frederich M. Ausubel, et al., *Current Protocols in Molecular Biology*, Wiley Interscience, 1989). For example, the protein can be expressed in bacteria as GST-fusion protein and purified by glutathione agarose beads (Sigma) as described (Erangionic and Neel, *Analytical Biochemistry*, 210:179, 1993). Alternatively, the protein can be expressed as a secretory product in mammalian cells and purified from conditioned medium (Cadena and Gill, *Protein Expression and Purification* 4:177, 1993).

The invention also provides polynucleotides which encode the hIR endocytic code binding polypeptide of the invention and the synthetic peptide of Sequence ID No.3. As used herein, "polynucleotide" refers to a polymer of deoxyribonucleotides or ribonucleotides, in the form of a separate fragment or as a component of a larger construct. DNA encoding the polypeptide of the invention can be assembled from cDNA fragments or from oligonucleotides which provide a synthetic gene which is capable of being expressed in a recombinant transcriptional unit. Polynucleotide sequences of the invention include DNA, RNA and cDNA sequences.

DNA sequences of the invention can be obtained by several methods. For example, the DNA can be isolated using hybridization procedures which are well known in the art. These include, but are not limited to: 1) hybridization of probes to genomic or cDNA libraries to detect shared nucleotide sequences; 2) antibody screening of expression libraries to detect shared structural features and 3) synthesis by the polymerase chain reaction (PCR).

Hybridization procedures are useful for the screening of recombinant clones by using labeled mixed synthetic oligonucleotide probes where each probe is potentially the complete complement of a specific DNA sequence in the hybridization sample which includes a heterogeneous mixture of denatured double-stranded DNA. For such screening, hybridization is preferably performed on either single-stranded DNA or denatured double-stranded DNA. Hybridization is particularly useful in the detection of cDNA clones derived from sources where an extremely low amount of mRNA sequences relating to the polypeptide of interest are present. In other words, by using stringent hybridization conditions directed to avoid non-specific binding, it is possible, for example, to allow the autoradiographic visualization of a specific cDNA clone by the hybridization of the target DNA to that single probe in the mixture which is its complete complement (Wallace, et al., *Nucleic Acid Research*, 9:879, 1981).

The development of specific DNA sequences encoding hIR endocytic code binding protein can also be obtained by: 1) isolation of double-stranded DNA sequences from the genomic DNA; 2) chemical manufacture of a DNA sequence to provide the necessary codons for the polypeptide of interest; and 3) in vitro synthesis of a double-stranded DNA sequence by reverse transcription of mRNA isolated from a eukaryotic donor cell. In the latter case, a double-stranded DNA complement of mRNA is eventually formed which is generally referred to as cDNA. Of these three methods for developing specific DNA sequences for use in recombinant procedures, the isolation of genomic DNA isolates is the least common. This is especially true when it is desirable to obtain the microbial expression of mammalian polypeptides due to the presence of introns.

The synthesis of DNA sequences is frequently the method of choice when the entire sequence of amino acid residues of the desired polypeptide product or smaller peptide is known. When the entire sequence of amino acid residues of the desired polypeptide is not known, the direct synthesis of DNA sequences is not possible and the method of choice is the synthesis of cDNA sequences. Among the standard procedures for isolating cDNA sequences of interest is the formation of plasmid- or phage-carrying cDNA libraries which are derived from reverse transcription of mRNA which is abundant in donor cells that have a high level of genetic expression. When used in combination with polymerase chain reaction technology, even rare expression products can be cloned. In those cases where significant portions of the amino acid sequence of the polypeptide are known, the production of labeled single or double-stranded DNA or RNA probe sequences duplicating a sequence putatively present in the target cDNA may be employed in DNA/DNA hybridization procedures which are carried out on cloned copies of the cDNA which have been denatured into a single-stranded form (Jay et al., *Nucl. Acid Res.* 11:2325, 1983).

A cDNA expression library, such as lambda gt11, can be screened indirectly for hIR endocytic code binding protein having at least one epitope, using antibodies specific for hIR endocytic code binding protein. Such antibodies can be either polyclonally or monoclonally derived and used to detect expression product indicative of the presence of hIR endocytic code binding protein cDNA.

In addition, a system previously described in yeast, the two-hybrid system (Zervos, et al., *Cell*, 72(2):223, 1993), can be used to identify clones which have DNA sequences encoding the polypeptide of the invention. The two hybrid system has been previously used to isolate interacting proteins. The system contains three classes of components: 1) the bait, a fusion protein containing site specific DNA binding domain and a protein domain of interest, and is known to be transcriptionally inert; b) two reporter genes, LexA op-LEU2 and LexAop-lacZ, that have no basal transcription level and that are bound by the bait; and c) the prey, the proteins encoded by an expression library, all of which are expressed as chimeras containing the nuclear location sequence from SV40 T antigen, the medium-strength activation domain carried on the B42 acid blob and the 12CA5 epitope tag from the influenza hemaglutinin protein. Conditional expression of the library encoded proteins is directed by a derivative of the GAL1 promoter. The host strain contains the LexAop-LEU 2 construction which allows cells that contain interacting proteins to be selected by growth on medium that lacks leucine. The lexAop-lacZ reporter allows LEU+cells to be quickly screened to confirm the interaction.

A polynucleotide sequence can be deduced from the genetic code, however, the degeneracy of the code must be taken into account. Polynucleotides of the invention include sequences which are degenerate as a result of the genetic code. There are 20 natural amino acids, most of which are specified by more than one codon. Therefore, as long as the amino acid sequence of hIR endocytic code binding protein results in a functional polypeptide (at least, in the case of the sense polynucleotide strand), all degenerate nucleotide sequences are included in the invention.

The polynucleotide sequence for hIR endocytic code binding protein also includes sequences complementary to the polynucleotide encoding hIR endocytic code binding protein (antisense sequences). Antisense nucleic acids are DNA or RNA molecules that are complementary to at least a portion of a specific mRNA molecule (Weintraub, *Scientific American*, 262:40, 1990). The invention embraces all antisense polynucleotides capable of inhibiting production of hIR endocytic code binding protein. In the cell, the antisense nucleic acids hybridize to the corresponding mRNA, forming a double-stranded molecule. The antisense nucleic acids interfere with the translation of the mRNA since the cell will not translate a mRNA that is double-stranded. Antisense oligomers of about 15 nucleotides are preferred, since they are easily synthesized and are less likely to cause problems than larger molecules when introduced into the target hIR endocytic code binding protein-producing cell. The use of antisense methods to inhibit the in vitro translation of genes is well known in the art (Marcus-Sakura, *Anal. Biochem.*, 172:289, 1988).

In addition, ribozyme nucleotide sequences for hIR endocytic code binding protein are included in the invention. Ribozymes are RNA molecules possessing the ability to specifically cleave other single-stranded RNA in a manner analogous to DNA restriction endonucleases. Through the modification of nucleotide sequences which encode these RNAs, it is possible to engineer molecules that recognize specific nucleotide sequences in an RNA molecule and cleave it (Cech, *J. Amer. Med. Assn.*, 260:3030, 1988). A major advantage of this approach is that, because they are sequence-specific, only mRNAs with particular sequences are inactivated.

There are two basic types of ribozymes namely, tetrahymena-type (Hasselhoff, *Nature*, 334:585, 1988) and "hammerhead"-type. Tetrahymena-type ribozymes recognize sequences which are four bases in length, while "hammerhead"-type ribozymes recognize base sequences 11–18 bases in length. The longer the recognition sequence, the greater the likelihood that that sequence will occur exclusively in the target mRNA species. Consequently, hammerhead-type ribozymes are preferable to tetrahymena-type ribozymes for inactivating a specific mRNA species and 18-based recognition sequences are preferable to shorter recognition sequences.

Antibodies provided in the present invention are immunoreactive or bind to hIR endocytic code binding protein. Antibodies of the invention also include antibodies which bind to the synthetic peptide in Sequence ID No.3. Antibody which consists essentially of pooled monoclonal antibodies with different epitopic specificities, as well as distinct monoclonal antibody preparations are provided. Monoclonal antibodies are made from antigen containing fragments of the protein by methods well known in the art (Kohler, et al., *Nature*, 256: 495, 1975; *Current Protocols in Molecular Biology*, Ausubel, et al., ed., 1989).

Antibodies which bind to the hIR endocytic code binding protein of the invention can be prepared using an intact polypeptide or fragments containing small peptides of interest as the immunizing antigen. The polypeptide, such as Sequence ID No. 2, or a peptide, such as Sequence ID No.3 can be used to immunize an animal, and can be derived from translated cDNA or chemical synthesis and is purified and conjugated to a carrier protein, if desired. Such commonly used carriers which are chemically coupled to the peptide include keyhole limpet hemocyanin (KLH), thyroglobulin, bovine serum albumin (BSA), and tetanus toxoid. The coupled peptide is then used to immunize the animal (e.g., a mouse, a rat, or a rabbit).

If desired, polyclonal antibodies can be further purified, for example, by binding to and elution from a matrix to which the polypeptide or a peptide to which the antibodies were raised is bound. Those of skill in the art will know of various techniques common in the immunology arts for purification and/or concentration of polyclonal antibodies, as well as monoclonal antibodies (See for example, Coligan, et al., Unit 9, *Current Protocols in Immunology*, Wiley Interscience, 1991, incorporated by reference).

It is also possible to use the anti-idiotype technology to produce monoclonal antibodies which mimic an epitope. For example, an anti-idiotypic monoclonal antibody made to a first monoclonal antibody will have a binding domain in the hypervariable region which is the "image" of the epitope bound by the first monoclonal antibody. Thus, in the present invention, an anti-idiotype antibody produced from an antibody which binds to the synthetic peptide of the invention can bind to the endocytic code site on hIR which binds with the protein of the invention, thereby preventing hIR endocytic code binding protein from binding to hIR.

Polynucleotide sequences encoding the hIR endocytic code binding protein or synthetic peptide (Sequence ID No. 3) of the invention can be expressed in either prokaryotes or eukaryotes. Hosts can include microbial, yeast, insect and mammalian organisms. Methods of expressing DNA sequences having eukaryotic or viral sequences in prokaryotes are well known in the art. Biologically functional viral and plasmid DNA vectors capable of expression and replication in a host are known in the art. Such vectors are used to incorporate DNA sequences of the invention.

DNA sequences encoding the polypeptides can be expressed in vitro by DNA transfer into a suitable host cell. "Host cells" are cells in which a vector can be propagated and its DNA expressed. The term also includes any progeny of the subject host cell. It is understood that all progeny may not be identical to the parental cell since there may be mutations that occur during replication. However, such progeny are included when the term "host cell" is used. Methods of stable transfer, in other words when the foreign DNA is continuously maintained in the host, are known in the art.

In the present invention, the hIR endocytic code binding protein polynucleotide sequences may be inserted into a recombinant expression vector. The term "recombinant expression vector" refers to a plasmid, virus or other vehicle known in the art that has been manipulated by insertion or incorporation of the genetic sequences. Such expression vectors contain a promoter sequence which facilitates the efficient transcription of the inserted genetic sequence of the host. The expression vector typically contains an origin of replication, a promoter, as well as specific genes which allow phenotypic selection of the transformed cells. Vectors suitable for use in the present invention include, but are not limited to the T7-based expression vector for expression in bacteria (Rosenberg et al., *Gene* 56:125, 1987), the pMSXND expression vector for expression in mammalian cells (Lee and Nathans, *J. Biol. Chem.* 263:3521, 1988) and baculovirus-derived vectors for expression in insect cells. The DNA segment can be present in the vector operably linked to regulatory elements, for example, a promoter (e.g., T7, metallothionein I, or polyhedrin promoters).

The vector may include a phenotypically selectable marker to identify host cells which contain the expression vector. Examples of markers typically used in prokaryotic expression vectors include antibiotic resistance genes for ampicillin (β-lactamases), tetracycline and chloramphenicol (chloramphenicol acetyltransferase). Examples of such markers typically used in mammalian expression vectors include the gene for adenosine deaminase (ADA), aminoglycoside phosphotransferase (neo, G418), dihydrofolate reductase (DHFR), hygromycin-B-phosphotransferase (HPH), thymidine kinase (TK), and xanthine guanine phosphoribosyltransferse (XGPRT, gpt).

Transformation of a host cell with recombinant DNA may be carried out by conventional techniques which are well known to those skilled in the art. Where the host is prokaryotic, such as *E. coli*, competent cells which are capable of DNA uptake can be prepared from cells harvested after exponential growth phase and subsequently treated by the $CaCl_2$ method by procedures well known in the art. Alternatively, $MgCl_2$ or RbCl can be used. Transformation can also be performed after forming a protoplast of the host cell or by electroporation.

When the host is a eukaryote, such methods of transfection of DNA as calcium phosphate co-precipitates, conventional mechanical procedures such as microinjection, electroporation, insertion of a plasmid encased in liposomes, or virus vectors may be used. Eukaryotic cells can also be cotransformed with DNA sequences encoding the polypeptides of the invention, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein. (*Eukaryotic Viral Vectors*, Cold Spring Harbor Laboratory, Gluzman ed., 1982). Examples of mammalian host cells include COS, BHK, 293, and CHO cells.

Isolation and purification of host cell expressed polypeptide, or fragments thereof, provided by the invention, may be carried out by conventional means including preparative chromatography and immunological separations involving monoclonal or polyclonal antibodies.

The hIR endocytic code binding protein of the invention is useful in a screening method for identifying compounds or compositions which affect the binding of the hIR endocytic code binding protein. Thus, in another embodiment, the invention provides a method for identifying a composition which affects the binding of a polypeptide to the endocytic code of a cell surface receptor comprising incubating the components, which include the composition to be tested, the polypeptide, and the endocytic code, under conditions sufficient to allow the components to interact, then subsequently measuring the effect the composition has on the binding of the polypeptide to the endocytic code. The observed effect on the binding of the polypeptide to a cell receptor endocytic code may be either inhibitory or enhancement of binding. Preferably, the endocytic code is from insulin receptor and the polypeptide is the polypeptide according to Sequence ID No.2 or the synthetic peptide according to Sequence ID No.3. Methods for measuring the effect of the composition on the binding of a polypeptide to the endocytic code of a cell surface receptor will be known to those of skill in the art. For example, the effect of binding of the hIR endocytic code binding protein to hIR can be analyzed by measuring internalization of radiolabelled insulin (e.g. $^{125}$I-insulin) or photoaffinity-labeled insulin receptors.

In another embodiment, the invention provides a method of treating a cell disorder associated with endocytosis of the insulin receptor, comprising administering to a subject with the disorder a therapeutically effective amount of reagent which modulates the activity of the endocytic code of the receptor. Preferably, the subject is a human. The term "therapeutically effective" means that the amount of monoclonal antibody, anti-idiotype antibody or antisense nucleotide, for example, which is used, is of sufficient quantity to ameliorate the endocytosis, or hIR endocytic code binding protein-associated disorder. Preferably, the disorder which is treated is diabetes. Essentially, any disorder which is etiologically linked to hIR endocytic code binding protein would be considered susceptible to treatment.

Treatment includes administration of a reagent which modulates hIR endocytic code binding protein binding to hIR. The term "modulate" envisions the inhibition of hIR endocytic code binding protein binding to hIR when it is desirable to decrease hIR endocytosis and increase the concentration of insulin receptors on the surface of the cell. Augmentation of hIR endocytic code binding protein binding to hIR is desirable to increase endocytosis of the insulin receptor. Suppression of binding of the hIR binding polypeptide may be accomplished, for example, by using the peptide of Sequence ID No.3 as a competitive inhibitor of the natural hIR endocytic code binding site in a cell. When a cell disorder is associated with hIR endocytic code binding protein overexpression, such suppressive reagents as antisense hIR endocytic code binding protein polynucleotide sequence or hIR endocytic code binding protein binding antibody can be introduced to a cell. In addition, an anti-idiotype antibody which binds to a monoclonal antibody which binds a peptide of the invention may also be used in the therapeutic-method of the invention. Alternatively, when a cell proliferative disorder is associated with under-expression or expression of a mutant hIR endocytic code binding protein polypeptide, a sense polynucleotide sequence (the DNA coding strand) or hIR endocytic code binding protein polypeptide can be introduced into the cell.

The antibodies of the invention can be administered parenterally by injection or by gradual infusion over time. The monoclonal antibodies of the invention can be administered intravenously, intraperitoneally, intramuscularly, subcutaneously, intracavity, or transdermally.

Preparations for parenteral administration of a peptide or an antibody of the invention include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, antioxidants, chelating agents, and inert gases and the like.

Another targeted delivery system for hIR endocytic code binding protein polynucleotides is a colloidal dispersion system. Colloidal dispersion systems include macromolecule complexes, nanocapsules, microspheres, beads, and lipid-based systems including oil-in-water emulsions, micelles, mixed micelles, and liposomes. The preferred colloidal system of this invention is a liposome. Liposomes are artificial membrane vesicles which are useful as delivery vehicles in vitro and in vivo. It has been shown that large unilamellar vesicles (LUV), which range in size from 0.2–4.0 um can encapsulate a substantial percentage of an aqueous buffer containing large macromolecules. RNA, DNA and intact virions can be encapsulated within the aqueous interior and be delivered to cells in a biologically active form (Fraley, et al., *Trends Biochem. Sci.*, 6:77, 1981). In addition to mammalian cells, liposomes have been used for delivery of polynucleotides in plant, yeast and bacterial cells. In order for a liposome to be an efficient gene transfer vehicle, the following characteristics should be present: (1) encapsulation of the genes of interest at high efficiency while not compromising their biological activity; (2) preferential and substantial binding to a target cell in comparison to non-target cells; (3) delivery of the aqueous contents of the vesicle to the target cell cytoplasm at high efficiency; and (4) accurate and effective expression of genetic information (Mannino, et al., *Biotechniques*, 6:682, 1988).

The targeting of liposomes has been classified based on anatomical and mechanistic factors. Anatomical classification is based on the level of selectivity, for example, organ-specific, cell-specific, and organelle-specific. Mechanistic targeting can be distinguished based upon whether it is passive or active. Passive targeting utilizes the natural tendency of liposomes to distribute to cells of the reticuloendothelial system (RES) in organs which contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization.

The invention also provides a method for detecting a polypeptide which binds to the endocytic code of the human insulin receptor comprising contacting a sample comprising a cell component associated with binding to the endocytic code of the receptor with a reagent which binds to the component and measuring the interaction of the reagent with the component. The cell component can be nucleic acid, such as DNA or RNA, or protein. When the component is nucleic acid, the reagent is a nucleic acid probe or PCR primer. The interaction of a nucleic acid reagent with a nucleic acid encoding a polypeptide which binds to the endocytic code of hIR is typically measured using radioactive labels, however, other types of labels will be known to those of skill in the art. When the cell component is protein, the reagent is typically an antibody probe. The probes are detectably labeled, for example, with a radioisotope, a fluorescent compound, a bioluminescent compound, a chemiluminescent compound, a metal chelator or an enzyme. Those of ordinary skill in the art will know of other suitable labels for binding to the antibody, or will be able to ascertain such, using routine experimentation. Such cells which are preferably used in the method of detection described above are neuronal cells. Specifically, in light of the high level of expression of the endocytic code binding protein of the invention in neuroblastoma cells, the method of the invention is useful for the detection and identification of a neuroblastoma cell.

The endocytic code of the hIR used in the method of detection of a hIR endocytic code binding protein described above may exist as a single protein unit or a fusion protein. The fusion protein preferably consists of exon 16 of hIR and glutathione-S-transferase (GST) as a carrier protein. The nucleotide sequence is cloned 3' to the carrier protein in an expression vector, such as pGEX or such derivatives as pGEX2T or pGEX3X, the gene is expressed, the cells are lysed, and the extract is poured over a column containing a resin or mixed directly with a resin to which the carrier protein binds. When GST is the carrier, a glutathione (GSH) resin is used. When maltose-binding protein (MBP) is the carrier, an amylose resin is used. Other carrier proteins and the appropriate binding resin will be known to those of skill in the art. A cell extract suspected of containing an endocytic code binding protein of the invention is mixed with the glutathione resin-exon 16 mixture and binding is detected as described above.

The materials of the invention are ideally suited for the preparation of a kit useful for the detection of the level of hIR endocytic code binding protein in a cell. The kit comprises an antibody which binds an endocytic code binding protein which binds to the endocytic code of the human insulin receptor, the kit comprising a carrier means being compartmentalized to receive in close confinement therein one or more containers such as vials, tubes, and the like, each of the container means comprising one of the separate elements to be used in the assay. For example, one of the container means may comprise a monoclonal antibody of the invention which is, or can be, detectably labelled. The kit may also have containers containing buffer(s) and/or a container comprising a reporter-means, such as a biotinbinding protein, such as avidin or streptavidin, bound to a reporter molecule, such as an enzymatic, or fluorescent label.

The following examples are intended to illustrate but not limit the invention. While they are typical of those that might be used, other procedures known to those skilled in the art may alternatively be used.

EXAMPLES

The present invention provides a protein that binds specifically to the functionally defined endocytic codes of hIR. The two hybrid system in yeast was utilized for isolation of the gene encoding this protein (Zervos, et al., *Cell*, 72(2):223, 1993).

Ligand-induced endocytosis of human insulin receptor (hIR) requires both intrinsic protein tyrosine kinase and sequences encoded by exon 16. To identify cellular components mediating receptor endocytosis, exon 16, which encodes 22 amino acids, was fused to truncated Lex A and the fusion protein was used to screen a HeLa cell expression library using a two hybrid system in yeast. One candidate was isolated from $10^5$ individual transformants, and the partial clone was used to isolate the full length 1.73 kb cDNA. The endocytosis code binding protein, whose sequence is unique in the data bases, contains a glycine-rich domain and potential sites for tyrosine phosphorylation. The binding site was localized to the C-terminal 7 kDa (SEQUENCE ID NO. 3). An immobilized GST-7 kDa fusion protein was demonstrated to bind partially purified hIR in vitro. This protein recognized the strong code GPLY and to a lesser extent the weaker code NPEY. Mutation of GPLY in hIR exon 16 to APLA abolished binding while mutation of NPEY to APEA reduced binding by about 30%. The protein recognized the exon 16 equivalent in IGF-1 receptors weakly but did not recognize endocytic codes in EGF, LDL and transferrin receptors. Northern and Western blotting indicated that this gene is widely expressed in human cells and highly expressed in two neuroblastoma cell lines. This novel protein interacts specifically with endocytic codes of hIR.

Figure 1B:
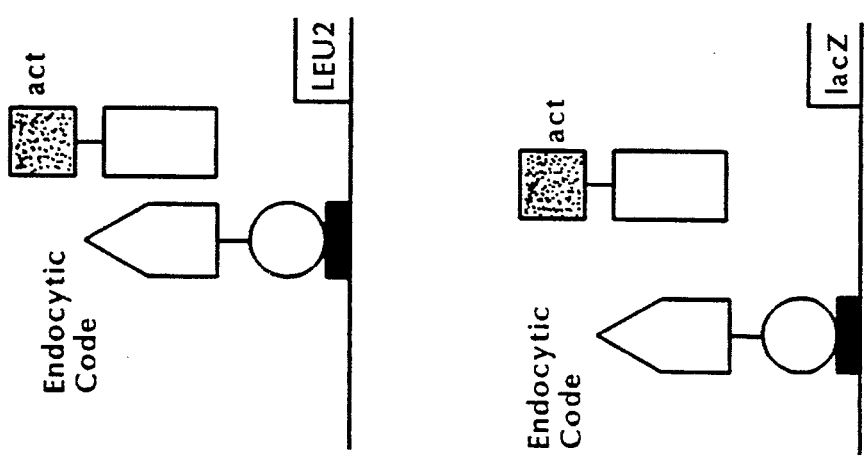
Figure 1C:
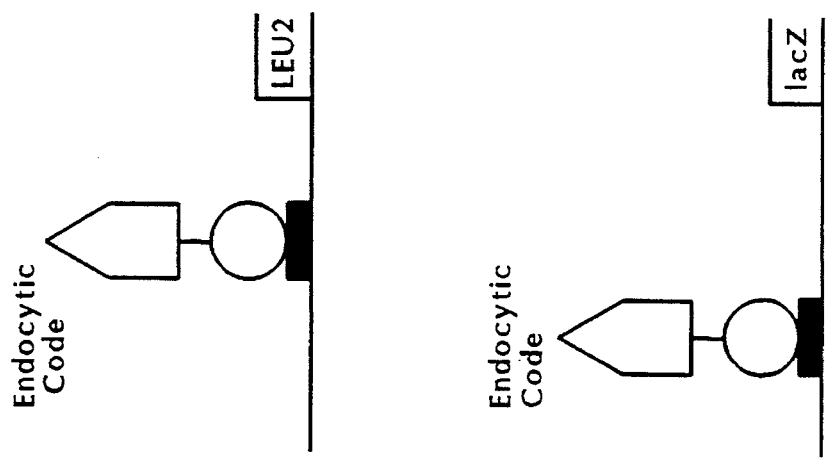

The two hybrid system has been previously used to isolate interacting proteins. The system contains three classes of components: a) the bait, a fusion protein containing a site specific DNA binding domain and a protein domain of interest, and is known to be transcriptionally inert; b) two reporter genes, LexA op-LEU2 and LexAop-lacZ, that have no basal transcription level and that are bound by the bait; and c) the prey, the proteins encoded by an expression library, all of which are expressed as chimeras containing the nuclear location sequence from SV40 T antigen, the medium-strength activation domain carried on the B42 acid blob and the 12CA5 epitope tag from the influenza hemaglutinin protein. Conditional expression of the library encoded proteins is directed by a derivative of the GAL1 promoter. The host strain contains the LexAop-LEU 2 construction which allows cells that contain interacting proteins to be selected by growth on medium that lacks leucine. The lexAop-lacZ reporter allows LEU+cells to be quickly screened to confirm the interaction. An outline of the two hybrid system is shown in FIG. 1A–C.

EXAMPLE 1

ISOLATION OF A CELLULAR COMPONENT WHICH BINDS TO THE ENDOCYTIC CODE OF THE HUMAN INSULIN RECEPTOR (HIR)

The yeast strain EGY48 (Zervos, et al., *Cell*, 72:(2)223, 1993) that contains both the LexAop-LEU2 and LexAop-lacZ reporter, as well as a plasmid that directs synthesis of the LexA-Exon 16 of hIR bait, was utilized in the two hybrid system. Two oligos were synthesized to amplify exon 16 of the human insulin receptor by the polymerase chain reaction (PCR). The oligonucleotides were: 5'-TTTAGAATTC-CAGCCAGATGGGCCGC-3' (SEQUENCE ID NO. 4) and 5'-CGATGGATCCATCACTGGCACTGAGA-3' (SEQUENCE ID NO. 5). The PCR reaction procedures were carried out by denaturing the oligonucleotides and templates at 94° C. for 1.5 minutes, annealing them at 55° C. for 1.0 minutes and extending the reaction at 72° C. for 1.0 minutes. Following 30 cycles of amplification, the PCR product was digested with EcoRI and BamHI restriction enzymes. The PCR product was an 80 base pair DNA fragment which was then ligated into the pEG202 vector at the EcoRI and BamHI sites. The fusion plasmid directed synthesis of the LexA-exon 16 of the hIR bait. Bait plasmids which contain mutations at exon 16 were constructed using the same pair of oligos except using the mutant template DNA for the PCR. In addition, mutant hIR cDNAs that encode changes in exon 16 were used as a template so that amino acids $G^{950}$ PLY (SEQUENCE ID NO. 6) became APLA (SEQUENCE ID NO. 7) and $N^{957}$ PEY (SEQUENCE ID NO. 8) became APEA (SEQUENCE ID NO. 9) in the encoded protein (Rajagopalan, et al., *J. Biol. Chem.*, 266(34):230–68, 1991).

LexA-exon16 was shown to be transcriptionally inactive and to be able to bind to the LexAop-lacZ reporter. The interaction or PREY expression library was prepared as a HeLa cell cDNA library in the vector pJG 4–5 (Zervos, et al., *Cell*, 72(2):223, 1993) and was introduced into the yeast strain EGY48; $1\times10^6$ transformants were isolated. One-third of these are expected to express fusion protein in the correct reading frame. A dilution of the pooled colonies were grown in liquid culture in the presence of galactose to induce the synthesis of the library encoded protein. The colonies were diluted again so that each original transformant was represented about 20 times, and then the cells were plated on galactose-containing medium without leucine. From $2\times10^7$ cells, 398 LEU+colonies were isolated. Three of these were reported as blue only on galactose Xgal, but not on glucose Xgal medium, confirming that they required the library encoded protein to bind and therefore for survival.

Plasmid DNAs from these positive colonies were rescued as described (Hoffman and Winston, *Gene*, 57:267 1987), introduced into the bacterial strain KC8 (Dr. Grace Gill, University of California, Berkeley) and transformants were collected on trp-ampicillin plates. Plasmid DNAs were isolated from these cells using the Magic miniprep DNA purification system (Promega). The plasmid DNAs were digested by EcoR1 and Xho1 to release the DNA inserts and were shown to have DNA inserts with 500 base pair length. After triple digestion with EcoR1, Xho1 and HaeIII, the DNA plasmids were analyzed on 1.8% agarose 0.5×TBE gels. The same pattern was observed for each.

The 500 bp DNA fragment which encodes a 7 kDa peptide was isolated from the plasmid by EcoRI and Xho1 restriction enzymes. To prepare the fragment for cloning as a bacterial fusion protein, it was first cloned into pBluescript (Stratagene) at EcoRI and Xho1 sites. The 500 bp DNA insert was excised from the fusion pBluescript plasmid by BamHI and Xho1 enzymes. This BamHI and Xho1 DNA fragment was ligated into pGEX-KG (Pharmacia) in frame at BamHI and Xho1 sites. This plasmid was used to produce a glutathione-S-transferase-7 kDa fusion protein in bacteria.

Western blotting analysis with anti-hemaglutinin antiserum 12CA5 from bacteria verified that the library plasmid directed the synthesis of a 28 kDa fusion protein (FIG. 2b). The known amino terminus of the fusion protein was 21 kDa, therefore, the library encoded protein was 7 kDa. An antibody generated against the GST-7 kDa fusion protein recognized the same 28 kDa protein in yeast that expressed the isolated library plasmid (FIG. 2c). 500 bp DNA fragments from the three positive colonies were cloned into pBlueScript (Stratagene) and sequenced using dideoxynucleotide chain termination and Sequenase (U.S. Biochemical) and shown to have the same sequence.

The cloned DNA insert from one of the antisera positive clones was used as probe for Northern blot analysis with total RNA from 12 different cell lines. HeLa, HepG2, ATT20, SKNMC, F9, PC12, RAT1, CV1, N18, SKNSH, IMR32, Jurkat and four mouse tissues, liver, kidney, cortex and lung were obtained from ATCC (Rockville, Md.) and from Dr. Eric Turner (University of California, San Diego). Northern blot analysis demonstrated that the gene for the exon 16 binding protein is widely expressed in human cells and highly expressed in two neuroblastoma cell lines (SK-N-MC and SK-N-SH) (FIG. 3a). The messenger RNA is about 1.73 kb as seen in FIG. 3b.

The 500 bp DNA was excised from a positive clone and labelled with 32p using a random primer kit (U.S. Biochemical). This $^{32}$P-labelled DNA was used as a probe to screen a SK-N-MC lambda gtl 1 cDNA library by standard protocols (Molecular Cloning, A Laboratory Manual. eds. Sambrook, Fritsch, Maniatis, 1989, New York, Cold Spring Harbor Press). Phage DNAs were isolated from the eight positive colonies and the inserts were excised by EcoR1 digestion.

Southern blot analysis using the 8 clones showed that four of them contained the full length cDNA (FIG. 4). All four cDNA inserts were partially sequenced by dideoxy-nucleotide chain termination and sequenase (U.S. Biochemical) and were shown to be identical except for several base difference at both ends, indicating this gene existed in the genome. The complete sequenced 1.73 kb cDNA shares no homology in the gene data bases (e.g., GenBank, 79.0, EMBL 36, UGenBank 79-36, UEMBL36-79, GenBank-NEW10, EMBL-NEW10-2, PIR38, ENZYMES 9310).

Computer analysis allowed translation of the cDNA into the deduced amino acids, indicating a continuously open reading frame that encodes a 453 amino acid protein predicted to be approximately 50 kDa (FIGS. 5 and 6; SEQUENCE ID NOs. 1 and 2). The translated amino acid from the cDNA sequence showed several potential sites for tyrosine phosphorylation and a glycine-rich domain.

EXAMPLE 2

IMMUNOLOGICAL DETECTION OF A PROTEIN WHICH BINDS TO THE ENDOCYTIC CODE OF THE HIR

Two of the full length cDNAs from Example 1 were cloned into Bluescript plasmid (Stratagene) in both orientations. The two plasmid DNAs were then linearized and purified. Messenger RNA was transcribed using T3 or T7 RNA polymerases, and used in translation reactions (Translation in vitro, Protocols and Applications Guide, Promega, 1991 ). The reaction products were analyzed on a 10% SDS denaturing PAGE gel, and appeared as a 55–56 kDa protein (FIG. 7). This indicated that the open reading frame predicted from the cDNA sequences was consistent with the in vitro translation results.

The binding domain and the full length protein of the invention were expressed as glutathione-S-transferase (GST)-fusion proteins in BL21 bacterial cells by transformation. The GST-fusion protein was purified as described (Frangioni and Neel, Analytical Biochemistry, 210:179, 1993) and sent to Bethyl Laboratories, Inc., Montogmery, Tex. for immunization of one rabbit to generate antisera. 1×10$^7$ cells of SKNMC, HepG2 and HeLa were harvested and lysed into 1×SDS loading buffer. The cell lysates were run on 10% SDS PAGE gels and transferred to immobilon-P transfer membranes (Millipore). The filter was blotted with antisera using 1:10,000 dilution. HRP conjugated secondary Ab (Amersham) was used.

The antibody recognized an endogenous protein in the SKNMC cell extract in HepG2 cells and weakly detected a protein in the HeLa cell extract. This agrees with the Northern blot result (FIG. 3b; Example 2), which showed that the mRNA from the SK-N-MC cell was much more abundant than the mRNA from the HeLa cell (FIG. 8).

EXAMPLE 3

BINDING STUDIES OF THE ENDOCYTIC CODE RECOGNITION PROTEIN TO HIR

The protein recognized the strong code GPLY, and to a lesser extent, the weaker code NPEY in exon 16 of the hIR as defined by Rajagopalan, et al., (J. Biol. Chem., 266(34):23068, 1991) and by Backer, et al., (J. Cell Biol., 118(4):831, 1992) (FIG. 9). DNAs encoding a mutation of GPLY (SEQUENCE ID NO. 6) to APLA (SEQUENCE ID NO. 7) in hIR exon 16, mutation of NPEY (SEQUENCE ID NO. 8) to APEA (SEQUENCE ID NO. 9) and a double mutant containing both were cloned into the bait plasmid, PEG202 individually. PCR was used to amplify the DNA fragment encoding the endocytic code of each receptor (see oligos from Example 1). All of the endocytic codes were cloned into pEG202 at EcoRI and BamHI sites.

Interaction between the C-terminal region of the protein of the invention and the mutant exon 16 by hIR was determined by monitoring β-galactosidase activity on medium containing X-gal. Quantitative β-galactosidase assays were performed as described (Rose, M., et al., Methods in Yeast Genetics, Cold Spring Harbor Laboratory Press, 1990). The 7 kDa protein fragment corresponding to the carboxy terminus of the entire protein represents the site of interaction with exon 16 as determined in the initial isolation using the twohybrid system. The APLA mutant and double mutant failed to bind the protein while the APEA mutant still had 70% binding (FIG. 9). This result agrees with the in vivo data and shows that GPLY was a more dominant sequence for endocytosis than NPEY as defined by Rajagopalan, et al., supra.

The specificity of the interaction between the protein of the invention to other receptor endocytic codes was also studied by the two hybrid system. Small fragments containing the individual endocytic codes for the human EGF, IGF 1, LDL and transferrin receptor were cloned in the bait plasmid as described above and were shown to be transcriptionally inert (EGF-R:amino acid (aa) 993–1022, EGF-R:aa 1022–1186, Ullrich, et al., Nature, 309:418,1984; IGF1-R:aa 930–960, Ullrich, et al., EMBOJ, 5:2503, 1986; TfR:aa 1–61, McClelland and Ruddle, Cell, 39:267–274, 1984; LDL-R:aa 730–780 Yamamoto and Russel, Cell, 39:27–38, 1984). One pair of oligos were made corresponding to every receptor. Each Lex A fusion plasmid was then introduced into the yeast strain EGY48 that had the LexAop-lacZ reporter and the library plasmid pJG-4-5 that encoded the interaction domain. These cells were grown on galactose X-gal medium to detect the interaction between each endocytic code and the C-terminus of the protein of the invention. The protein recognized the exon 16 equivalent in IGF-1 receptors weakly but did not recognize the endocytic codes in EGF, LDL and transferrin receptors (See FIG. 9).

EXAMPLE 4

The fusion protein, GST-exon 16 binding protein can bind through its GST moiety to glutathione (GSH)-agarose beads. The 7 kDa GST-fusion protein and GST protein were immobilized on glutathione agarose beads and mixed with partially purified human insulin recepto at 4° C. The unbound receptor was then washed away and the bound receptor was detected by anti-hIR antibody. The 7 kDa protein precipitated the receptor (lanes 4–6) while the GST protein did not (lanes 1–3), indicating that the interaction between the hIR and 7 kDa GST-fusion protein was mediated by the 7 kDa fragment (FIG. 10).

Although the invention has been described with reference to the presently preferred embodiment, it should be understood that various modifications can be made without departing from the spirit of the invention. Accordingly, the invention is limited only by the following claims.

SEQUENCE ID LISTING

SEQUENCE ID NO. 1 is the nucleotide and deduced amino acid sequence for the endocytic code binding protein of the invention.

SEQUENCE ID NO. 2 is the deduced amino acid sequence for the endocytic code binding protein of the invention.

SEQUENCE ID NO. 3 is the amino acid sequence for the C-terminus of the endocytic code binding protein of the invention.

SEQUENCE ID NO. 4 is a nucleotide sequence for an oligonucleotide used in PCR of exon 16 of the human insulin receptor (hIR).

SEQUENCE ID NO. 5 is a nucleotide sequence for an oligonucleotide used in PCR of exon 16 of the human insulin receptor (hIR).

SEQUENCE ID NO. 6 is the amino acid sequence for an endocytic code of the hIR.

SEQUENCE ID NO. 7 is the amino acid sequence for an altered endocytic code of the hIR.

SEQUENCE ID NO. 8 is the amino acid sequence for an endocytic code of the hIR.

SEQUENCE ID NO. 9 is the amino acid sequence for an altered endocytic code of the hIR.

We claim:
1. An isolated polypeptide characterized by:
(a) binding to the endocytic code of the human insulin receptor; and
(b) having an amino acid sequence of SEQ ID NO:2.
2. An isolated peptide comprising SEQ ID NO:3.

* * * * *